United States Patent
Pike et al.

(10) Patent No.: US 6,592,697 B2
(45) Date of Patent: Jul. 15, 2003

(54) METHOD OF PRODUCING POST-CREPE STABILIZED MATERIAL

(75) Inventors: Richard Daniel Pike, Alpharetta, GA (US); Frank Paul Abuto, Duluth, GA (US); James Randall Morgan, Neenah, WI (US); Gregory Todd Sudduth, Cumming, GA (US); John Joseph Sayovitz, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 229 days.

(21) Appl. No.: 09/733,618

(22) Filed: Dec. 8, 2000

(65) Prior Publication Data

US 2003/0040242 A1 Feb. 27, 2003

(51) Int. Cl.$^7$ ................................................ B32B 31/00
(52) U.S. Cl. ..................... 156/183; 156/296; 156/308.4; 156/167
(58) Field of Search ................................ 156/183, 290, 156/308.4, 296, 167

(56) References Cited

U.S. PATENT DOCUMENTS

| | | | |
|---|---|---|---|
| 3,059,313 A | * | 10/1962 | Harmon ...................... 156/183 |
| 3,802,817 A | | 4/1974 | Matsuki et al. |
| 3,810,280 A | | 5/1974 | Walton et al. |
| 3,849,241 A | | 11/1974 | Butin et al. |
| 3,879,257 A | | 4/1975 | Gentile et al. |
| 3,903,342 A | | 9/1975 | Roberts, Jr. |
| 3,949,128 A | * | 4/1976 | Ostermeier ................. 153/183 |
| 4,000,237 A | | 12/1976 | Roberts, Jr. |
| 4,421,812 A | | 12/1983 | Plant |
| 4,422,892 A | | 12/1983 | Plant |
| 4,435,458 A | | 3/1984 | Hill |
| 5,108,820 A | | 4/1992 | Kaneko et al. |
| 5,108,827 A | | 4/1992 | Gessner |
| 5,336,552 A | | 8/1994 | Strack et al. |
| 5,382,400 A | | 1/1995 | Pike et al. |
| 5,674,590 A | | 10/1997 | Anderson et al. |
| 5,707,468 A | | 1/1998 | Arnold et al. |
| 5,814,390 A | | 9/1998 | Stokes et al. |
| 5,989,682 A | * | 11/1999 | Anderson ................... 156/209 |
| 6,001,303 A | | 12/1999 | Haynes et al. |
| 6,080,466 A | | 6/2000 | Yoshimura et al. |
| 6,087,551 A | * | 7/2000 | Pereira ....................... 604/358 |
| 6,150,002 A | | 11/2000 | Varona |

FOREIGN PATENT DOCUMENTS

| | | |
|---|---|---|
| EP | 586 924 | 3/1994 |
| WO | 97/19808 | 6/1997 |
| WO | WO 99/20821 | 4/1999 |
| WO | 99/22618 | 5/1999 |
| WO | 00/33780 | 6/2000 |

OTHER PUBLICATIONS

Manson, John A. and Sperling, Leslie H., *Polymer Blends & Composites*, Plenum Press, a division of Plenum Publishing Corp., New York, New York, pp. 273–277 (1976).

* cited by examiner

*Primary Examiner*—Jeff H. Aftergut
(74) *Attorney, Agent, or Firm*—Pauley Petersen Kinne & Erickson (57) ABSTRACT

A stabilized creped nonwoven web and a method for producing the same, wherein a creped nonwoven web is thermally stabilized, for example by through-air-bonding or embossing, to produce the stabilized creped nonwoven web. The stabilized creped nonwoven web having increased tensile strength in the machine direction and an enhanced appearance. The stabilized creped nonwoven web of this invention id capable of withstanding a tensile force or load in a machine direction of at least about 2.0 lbs. at 20% strain and a tensile force or load in the machine direction of at least about 5.0 lbs. at 50% strain.

18 Claims, 7 Drawing Sheets

METHOD OF PRODUCING POST-CREPE STABILIZED MATERIAL

FIELD OF THE INVENTION

This invention is directed to a post-crepe stabilized nonwoven material and a method of producing the same. More specifically, this invention is directed to a method of stabilizing a creped spunbond nonwoven web to provide increased tensile strength and enhanced appearance while minimizing the negative effects on bulk, permeability and other physical properties of the spunbond nonwoven web.

BACKGROUND OF THE INVENTION

Creped thermoplastic nonwoven materials and methods for creping the nonwoven materials are known in the art. For example, a conventional process for creping a raw nonwoven fabric begins with coating the nonwoven fabric with a lubricant and then pressing the nonwoven fabric between a drive roll and a plate having a rough sandpaper-like surface. The raw nonwoven fabric is crinkled in a wavelike fashion in the direction of movement of the fabric by the frictional force caused by the pressing. The resulting creped fabric has wavelike crepes which contribute to softness. However, such conventional creping processes are not believed to be permanent.

The "micropleat" structure of the creped fabric has a relatively low tensile modulus. As a result of this low tensile modulus, handling issues arise during the machine winding and the product conversion of the creped fabric. It is believed that the creping accomplished by conventional processes can be removed or reduced significantly by subjecting the creped fabric to mechanical stretching sufficient to flatten out the micropleat structure. Also, the creping is reduced during use of the fabric.

Thus, there is a need or desire for a creped thermoplastic nonwoven web having increased tensile strength sufficient to withstand the tensile or pulling forces experienced during the machine winding and product conversion processes.

There is also a need or desire for a method for producing a post-crepe stabilized nonwoven web with increased tensile strength and enhanced appearance without negatively effecting the bulk and permeability of the nonwoven web.

SUMMARY OF THE INVENTION

The present invention is directed to a stabilized creped nonwoven material or web having a limited extensibility in a machine direction and a method of producing the same. In accordance with this invention, the nonwoven web is creped and then thermally or heat stabilized. The stabilized creped nonwoven web has an increased tensile strength in a machine direction, which provides for easier machine winding and product conversion without damage to the nonwoven web due to tensile force or load associated with the machine winding and/or product conversion.

The stabilized creped nonwoven web of this invention is capable of withstanding a tensile force or load in a machine direction of at least about 2.0 lbs. at about 20% strain and a tensile force or load of at least about 5.0 lbs. at about 50% strain. Further, the thermal or heat stabilization process of this invention has minimal negative effect on the physical properties of the nonwoven web, for example bulk, permeability, and surface fiber loop structure. The thermally stabilized nonwoven web produced in accordance with this invention has an enhanced appearance due to the three-dimensional texture generated during a primary bonding step.

The method begins with providing any type of thermoplastic nonwoven web, including a spunbond web, a meltblown web, a bonded carded web, or a combination including any of the above. Desirably, the nonwoven web is a spunbond web.

The nonwoven web travels or moves through a primary bonder wherein the nonwoven web is thermally bonded, for example using a conventional calender roll. In accordance with one embodiment of this invention, the nonwoven web is thermally bonded using a Ramisch primary bond pattern. Any suitable conventional thermal bonding means may be used for thermally bonding the nonwoven web including, but not limited to, standard heat rolls, ultrasound and through-air-bonding.

After the nonwoven web is thermally bonded, the thermally bonded nonwoven web is creped. A first side of the nonwoven web may be creped using a first creping station wherein rollers nip the nonwoven web and guide it forward. As the rollers turn, a patterned or smooth printing roller dips into a bath containing an adhesive material, and applies the adhesive material to the first side of the nonwoven web. The adhesive-coated nonwoven web is then passed around a drying drum whereupon the adhesive-coated surface becomes adhered to the drying drum. The first side of the nonwoven web is then creped (i.e. lifted off the drum and bent) using the creping blade. Similarly, a second side of the nonwoven web may be creped using a second creping station, regardless of whether the first creping station has been bypassed.

The creped nonwoven web is passed through a post bonder wherein the creped nonwoven web is thermally or heat stabilized and wound onto a winding roll or storage roll. Post-crepe thermal or heat stabilization, including but not limited to through-air-bonding and embossing processes, produces the nonwoven web having improved stability and enhanced appearance while minimizing negative impacts on bulk, permeability, surface fiber loop structure and other physical properties of the nonwoven web.

The nonwoven web may be thermally stabilized using an embossing process. The creped nonwoven web is passed through a nip formed by an embossing or pattern roll and a smooth or second pattern roll. The pattern roll and/or the smooth roll may be heated using conventional means known to those having ordinary skill in the art. As the creped nonwoven web passes through the nip, the creped nonwoven web is. heated and embossed. Any suitable embossing pattern may be used to emboss the creped nonwoven web including a sine-wave embossing pattern, a machine direction ("MD") line embossing pattern, and a cross-stars embossing pattern. Embossing patterns such as the sine-wave embossing pattern and the MD line embossing pattern provide a continuous embossing pattern or bond in the machine direction and, thus, provide for a stronger material in the machine direction than patterns which are not continuous in the machine direction.

Alternatively, the nonwoven web may be thermally stabilized using a through-air-bonding process. Desirably, the nonwoven web in accordance with this embodiment is made of bicomponent fibers. The polymer components of the bicomponent fibers have different melting points. As the nonwoven web is passed through a through-air-bonder, heated air is forced through the nonwoven web and the lower melting polymer component melts to bond the nonwoven web. Desirably, the air is heated to a temperature greater than the melting temperature of the lower melting polymer component but less than the melting temperature of the other polymer component. The through-air-bonding process produces the thermally stabilized creped bicomponent nonwoven web.

The resulting thermally stabilized creped nonwoven web has low density, high permeability, excellent surface and bulk softness, recoverable stretch properties, surface topology, and permanent out-of-plane fiber orientation. The stabilized creped nonwoven web can be used in a variety of end products including liners, transfer and surge layers, outercovers, wipers, and other fluid handling materials.

With the foregoing in mind, it is a feature and advantage of the invention to provide a post-crepe stabilized nonwoven web having increased tensile strength to withstand the forces experienced during machine winding and product conversion.

It is another feature and advantage of the invention to provide a post-crepe stabilized nonwoven web which has limited extensibility in a machine direction.

It is another feature and advantage of the invention to provide a method for producing the post-crepe stabilized nonwoven web having increased tensile strength without compromising the physical properties of the nonwoven web, including bulk, permeability and surface fiber loop structure.

DEFINITIONS

"Crepe level" is a measure of creping and is calculated according to the following equation:

$$\text{Crepe level } (\%) = \frac{S_d - S_s}{S_d} \times 100; \quad \text{Eq. (1)}$$

wherein $S_d$ is the surface speed of the drying drum and $S_s$ is the surface speed of the storage roll.

"Bent out-of-plane" refers to a bonding or orientation of portions of the nonwoven web in a direction away from the plane in which the nonwoven web substantially lies before being subjected to the creping process. As used herein, the phrase "bent out-of-plane" generally refers to nonwoven webs having creped portions bent at least about 15 degrees away from the plane of the uncreped nonwoven web, preferably at least about 30 degrees.

"Looped" refers to unbonded filaments or portions of filaments in a creped nonwoven web which define an arch, semi-circle or similar configuration extending above the plane of the uncreped nonwoven web, and terminating at both ends in the nonwoven web (e.g. in the bonded areas of the creped nonwoven web).

"Nonwoven web" means a web having a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

"Nonwoven web bond pattern" is a pattern of interfilament bonding in the nonwoven web which is imparted during manufacture of the nonwoven web.

The term "meltblown fibers" means fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin and in U.S. Pat. No. 6,001,303 to Haynes, et al. Meltblown fibers are microfibers which may be continuous or discontinuous and are generally self bonding when deposited onto a collecting surface.

"Microfibers" means small diameter fibers having an average diameter not greater than about 100 microns, for example, having an average diameter of from about 0.5 microns to about 50 microns, or more particularly, an average diameter of from about 4 microns to about 40 microns.

"Spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 3,802,817 to Matsuki et al. and U.S. Pat. No. 5,382,400 to Pike et al. The disclosures of these patents are hereby incorporated by reference.

"Polymer" generally includes, but is not limited to, homopolymers, copolymers, such as, for example, block, graft, random and alternating copolymers, terpolymers, etc. and blends and modifications thereof. Furthermore, the term "polymer" shall include all possible geometrical configurations of the material. These configurations include, but are not limited to, isotactic, syndiotactic and random symmetries.

"Bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Strain" refers to a change in length of an object in a first direction per unit undistorted length in a direction, not necessarily the first direction.

"Tension" refers to a force tending to cause the extension of a body, or the balancing force within that body resisting the extension.

DETAILED DESCRIPTION OF THE PRESENTLY PREFERRED EMBODIMENTS

The present invention is directed to a stabilized creped nonwoven material or web 12 and a method of producing the same. In accordance with this invention, the nonwoven web 12 is creped and then thermally or heat stabilized to limit the extensibility of the nonwoven web 12 in a machine direction. The stabilized creped nonwoven web 12 has an increased tensile strength in a machine direction, which provides for easier machine winding and product conversion without damage to the nonwoven web 12 due to tensile forces or loads associated with the machine winding and/or product conversion processes.

The stabilized creped nonwoven web 12 of this invention is capable of withstanding a tensile force or load in a machine direction of at least about 2.0 lbs. at about 20% strain and a tensile force or load of at least about 5.0 lbs. at about 50% strain. Further, the thermal or heat stabilization process of this invention has minimal negative effect on the physical properties of the nonwoven web 12 such as bulk, permeability, and surface fiber loop structure. The thermal stabilized creped nonwoven web 12 of this invention has an enhanced appearance due to the three-dimensional texture generated during a primary bonding step.

Figure 1:
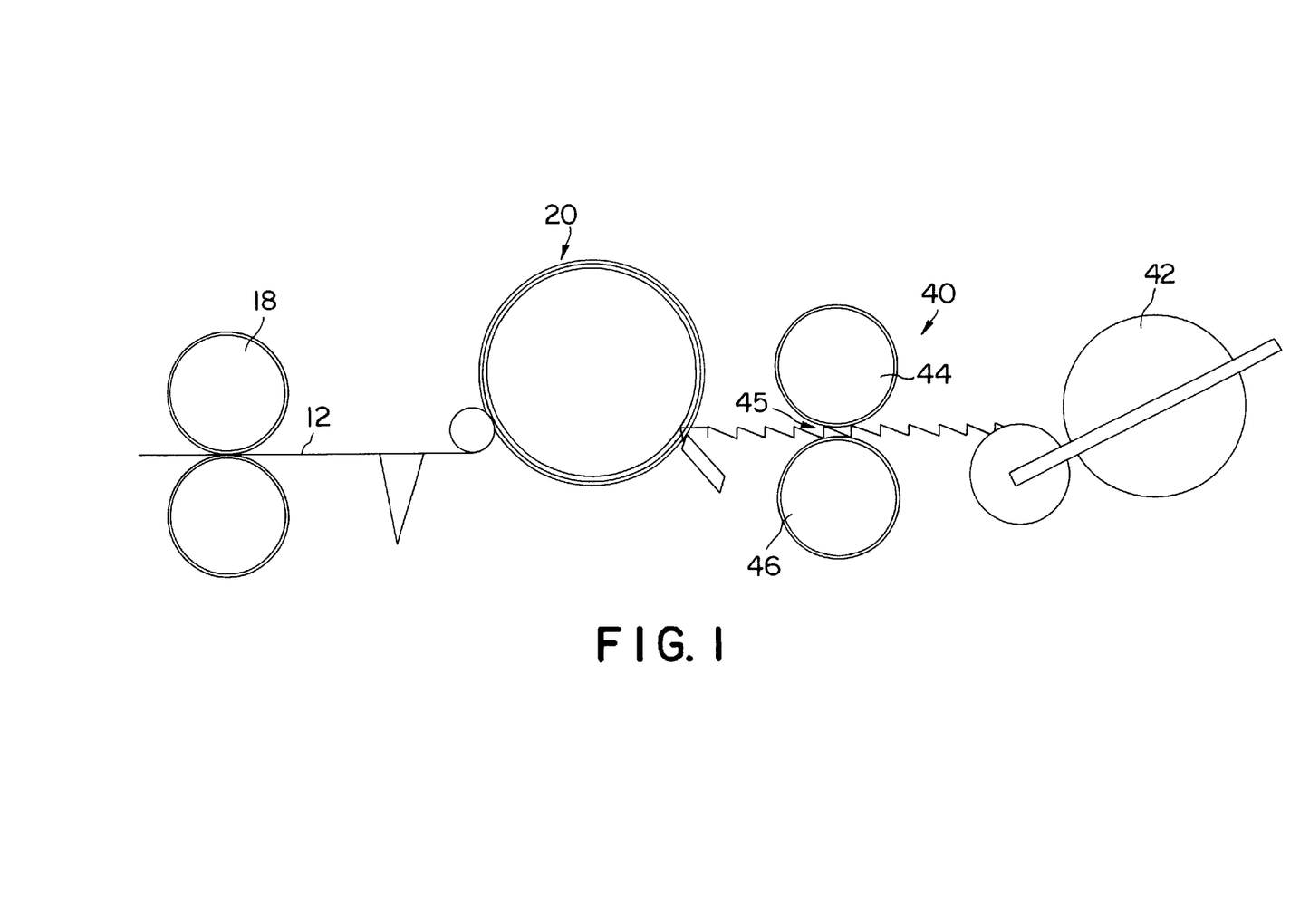
FIG. 1 illustrates schematically an apparatus for producing a stabilized creped nonwoven web, in accordance with one embodiment of this invention.

Referring to FIG. 1, there is schematically shown a method for producing the stabilized creped nonwoven web 12 in accordance with one embodiment of this invention. The method begins with providing a nonwoven web 12. In accordance with one embodiment of this invention, the nonwoven web 12 may be any type of thermoplastic nonwoven web. For instance, the nonwoven web 12 may be a spunbonded web, a meltblown web, a bonded carded web, or a combination including any of the above. Desirably, the nonwoven web 12 is a spunbonded web.

A wide variety of thermoplastic polymer materials can be used to make the nonwoven web 12. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers. The nonwoven web 12 desirably has a basis weight of about 0.2–2.0 ounces per square yard (osy) before creping, more desirably about 0.3–1.5 osy.

A web former (not shown) may provide or form the nonwoven web 12 using conventional web forming processes. Alternatively, an unwind spindle (not shown) may be provided from which the nonwoven web 12 is unwound and fed through a primary bonder 18.

Figure 2:
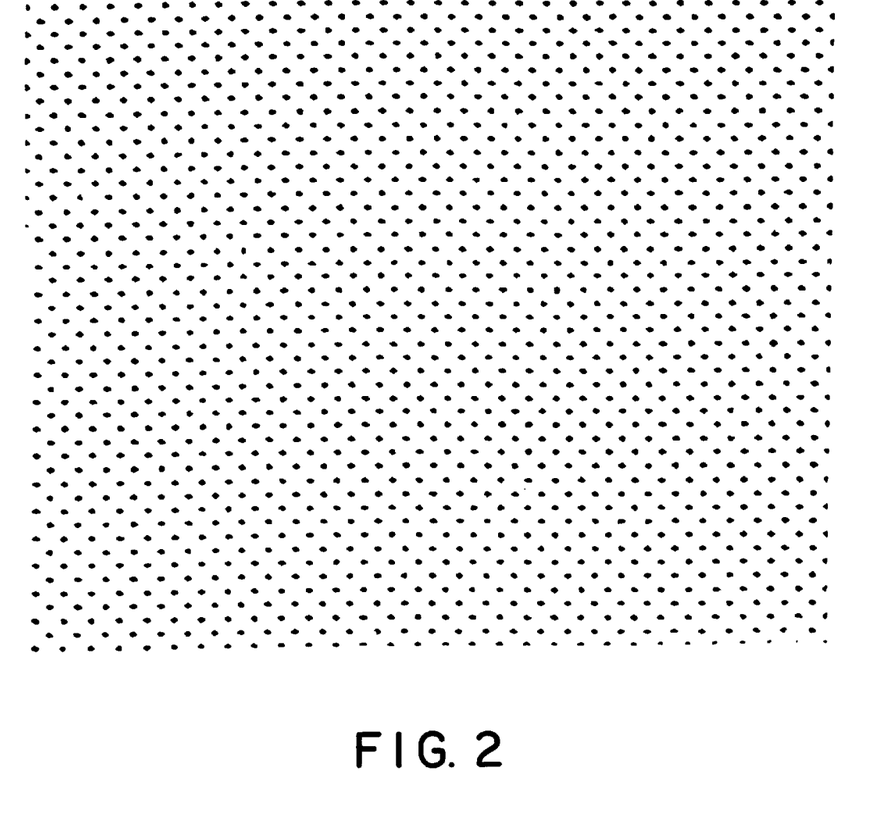
FIG. 2 illustrates a Ramisch primary bond pattern used to bond the nonwoven web, in accordance with one embodiment of this invention.

As the nonwoven web 12 travels or moves through the primary bonder 18, the nonwoven web 12 is thermally bonded, for example using a conventional calender roll. In accordance with one embodiment of this invention, the nonwoven web 12 is thermally bonded using a Ramisch primary bond pattern as shown in FIG. 2. The Ramisch primary bond pattern has a bond area of about 8% to about 14%, a pin density of about 52 pins/in$^2$, and a pin depth at 8% bond area of about 0.052 inch. The Ramisch primary bond pattern is a relatively deep, open pattern suitable for use in stretch applications. Any suitable conventional thermal bonding means may be used for thermally bonding the nonwoven web 12 including, but not limited to, standard heat rolls, ultrasound and through-air-bonding.

Figure 3:
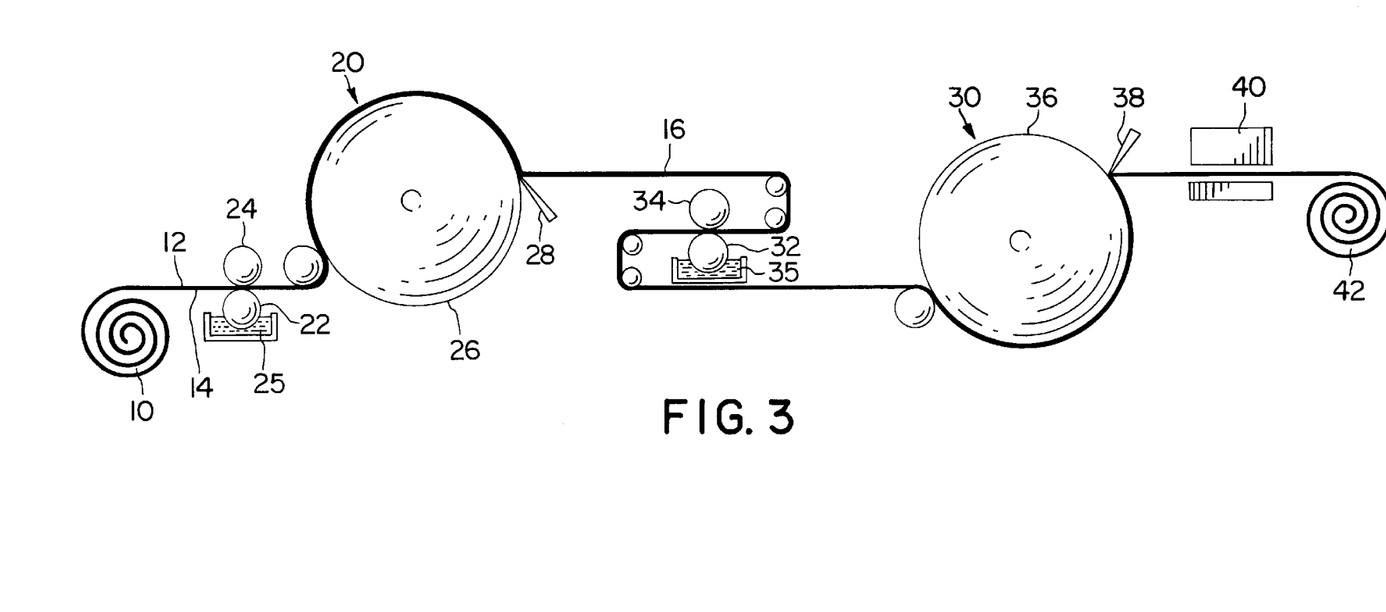
FIG. 3 illustrates schematically a creping apparatus for producing a creped nonwoven web, in accordance with one embodiment of this invention.

After the nonwoven web 12 is thermally bonded, the thermally bonded nonwoven web 12 is creped. As shown in FIGS. 1 and 3, the nonwoven web 12 may be passed through a first creping station 20 and/or a second creping station 30. If it is desired to crepe the nonwoven web 12 on only one side, the nonwoven web 12 may be passed through either the first creping station 20 or the second creping station 30, with one creping station being bypassed. If it is desired to crepe the nonwoven web 12 on both sides, the nonwoven web 12 may be passed through both the creping stations 20, 30.

As shown in FIG. 3, a first side 14 of the nonwoven web 12 may be creped using the first creping station 20. The first creping station 20 includes a first printing station having a lower patterned or smooth printing roller 22, an upper smooth anvil roller 24, and a printing bath 25, and also includes a drying drum 26 and an associated creping blade 28.

The rollers 22 and 24 nip the nonwoven web 12 and guide it forward. As the rollers 22 and 24 turn, the patterned or smooth printing roller 22 dips into a bath 25 containing an adhesive material, and applies the adhesive material to the first side 14 of the nonwoven web 12 in a partial coverage at a plurality of spaced apart locations, or in a total coverage. The adhesive-coated nonwoven web 12 is then passed around drying drum 26 whereupon the adhesive-coated surface 14 becomes adhered to the drying drum 26. The first side 14 of the nonwoven web 12 is then creped (i.e. lifted off the drum and bent) using the creping blade 28.

Desirably, but not necessarily, the nonwoven web 12 passes through a S-wrap system and a second side 16 of the nonwoven web 12 may be creped using the second creping station 30, regardless of whether the first creping station 20 has been bypassed. The second creping station 30 includes a second printing station having a lower patterned or smooth printing roller 32, an upper smooth anvil roller 34, and a printing bath 35, and also includes a drying drum 36 and an associated creping blade 38. The rollers 32 and 34 nip the nonwoven web 12 and guide it forward. As the rollers 32 and 34 turn, the printing roller 32 dips into a bath 35 containing adhesive material, and applies the adhesive material to the second side 16 of the nonwoven web 12 in a partial or total coverage. The adhesive-coated nonwoven web 12 is then passed around the drying drum 36 whereupon the adhesive-coated surface 16 becomes adhered to the drying drum 36. The second side 16 of the nonwoven web 12 is then creped (i.e. lifted off the drum surface and bent) using the creping blade 38.

After creping the nonwoven web 12, the creped nonwoven web 12 is passed through a post bonder 40 wherein the creped nonwoven web 12 is thermally stabilized and wound onto a winding roll or storage roll 42. The level of creping is affected by the surface speed of the storage roll 42 relative to the surface speed of the drying drum 36, according to Eq. (1) presented in "DEFINITIONS" above. The surface speed of the storage roll 42 is slower than the surface speed of the drying drum 36, and the difference between the two speeds affects the level of creping. The level of creping should generally be about 5–75%, desirably about 15–60%, more desirably about 25–50%. The creped nonwoven web 12 desirably has a basis weight of about 0.1 osy to about 4.0 osy, more desirably about 0.50 osy to about 1.0 osy.

A wide variety of adhesive bonding materials may be utilized to reinforce the fibers of the nonwoven web 12 at the locations of adhesive application, and to temporarily adhere the nonwoven web 12 to the surface of the drying drum 26 and/or 36. Elastomeric adhesives (i.e. materials capable of at least 75% elongation without rupture) are especially suitable. Suitable adhesive bonding materials include without limitation aqueous-based styrene butadiene adhesives, neoprene, polyvinyl chloride, vinyl copolymers, polyamides, and ethylene vinyl terpolymners. The presently desired adhesive material is an acrylic polymer emulsion sold by the B.F. Goodrich Company under the trade name HYCAR®. The adhesive material may be applied using the printing technique described above or may, alternatively, be applied by meltblowing, melt spraying, dripping, splattering, or any technique capable of forming a partial or total adhesive material coverage on the thermoplastic nonwoven web 12.

The percent adhesive material coverage of the nonwoven web 12 generally affects the level of creping obtained. Generally the adhesive material should cover about 5–100% of the nonwoven web surface, desirably about 10–70% of the nonwoven web surface, more desirably about 25–50% of the nonwoven web surface. In the presently desired embodiment, the nonwoven web 12 is coated with the adhesive material and creped on only one side. The nonwoven web 12 may be coated with the adhesive material and creped on both sides, however. The adhesive material should also penetrate the nonwoven web 12 in the locations where the adhesive material is applied. Generally, the adhesive material should penetrate through about 10–50% of the nonwoven web thickness, although there may be greater or less adhesive material penetration at some locations.

Post-crepe thermal or heat stabilization processes include but are not limited to through-air-bonding and embossing processes, which provide the nonwoven web 12 with increased tensile strength while minimizing the negative effect on bulk, permeability, surface fiber loop structure and other physical properties of the nonwoven web 12. Desirably, a bonding or embossing pattern produces a low bond area pattern which generates a plurality of land areas which are continuous in a machine direction.

In accordance with one embodiment of this invention, the nonwoven web 12 is thermally embossed to produce the thermally stabilized creped nonwoven web 12. As shown in FIG. 1, the creped nonwoven web 12 is passed through a nip 45 formed by an embossing or pattern roll 44 and a smooth roll 46. The pattern roll 44 and/or the smooth roll 46 are heated using conventional heating means, for example hot oil. Desirably, the pattern roll 44 and/or the smooth roll 46 are heated to a temperature of about 225° F. to about 375° F. The pattern roll 44 may be heated to a temperature which is the same or different than the temperature of the smooth roll 46. The bonding pressure of the nip 45 between the pattern roll 44 and the smooth roll 46 is desirably about 25 pounds per lineal inch (pli) to about 800 pli.

As the creped nonwoven web 12 passes through the nip 45, the creped nonwoven web 12 is heated and embossed. Any suitable embossing pattern may be used to emboss the creped nonwoven web 12. For example, a sine-wave embossing pattern having a pattern land area of about 9.6% and a pattern depth of about 0.090 inch (FIG. 4), a machine direction ("MD") line embossing pattern (FIG. 5) having a pattern land area of about 12.67% and a pattern depth of about 0.035 inch, and a cross-stars embossing pattern (FIG. 6) having a pattern bond area of about 17% and a pattern depth of about 0.035 inch, are suitable embossing patterns for thermally stabilizing the creped nonwoven web 12. The machine direction is indicated by arrow 99 on FIGS. 4, 5 and 6. Embossing patterns such as the sine-wave embossing pattern and the MD line embossing pattern provide a continuous embossing pattern or bond in the machine direction and, thus, provide for a stronger material in the machine direction than patterns which are not continuous in the machine direction.

Figure 4:
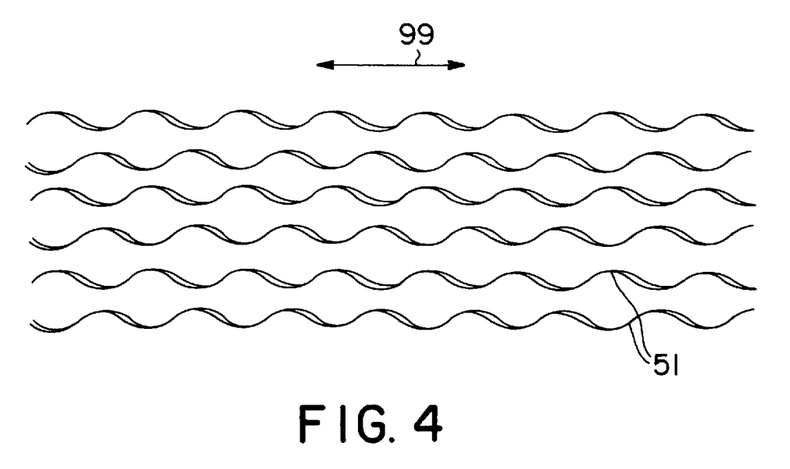
FIG. 4 illustrates a sine-wave embossing pattern used during the thermal stabilization of a creped nonwoven web, in accordance with one embodiment of this invention.
Figure 5:
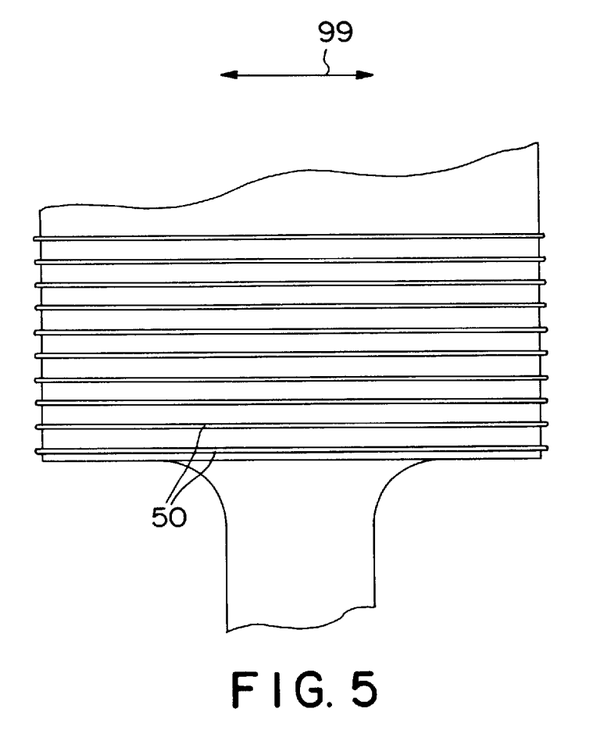
FIG. 5 illustrates a MD line embossing pattern used during the thermal stabilization of a creped nonwoven web, in accordance with one embodiment of this invention.
Figure 6:
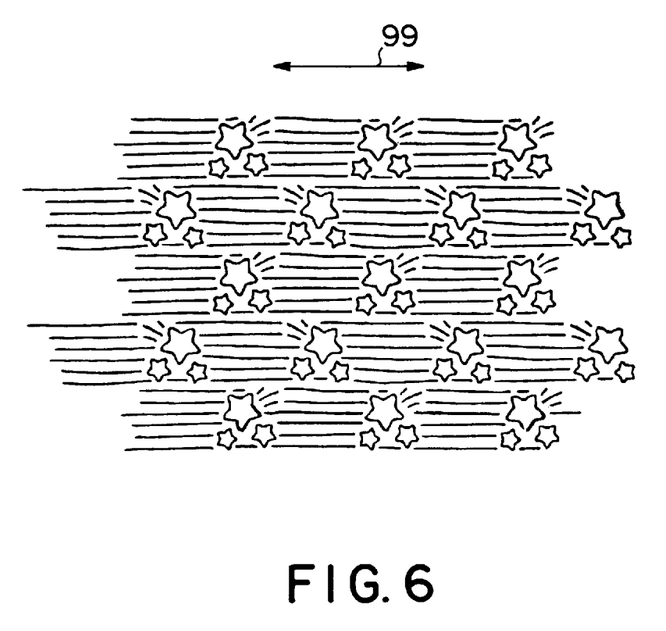
FIG. 6 illustrates a cross-stars embossing pattern used during the thermal stabilization of a creped nonwoven web, in accordance with one embodiment of this invention.

For example, the MD line pattern as shown in FIG. 5 has a plurality of embossing or bond lines 50 which are oriented in the machine direction and are generally spaced apart from adjacent bond lines 50 by about 0.140 inch to about 0.160 inch, desirably about 0.158 inch. Similarly, the sine-wave pattern as shown in FIG. 4 has a plurality of embossing or bond lines 51 which are oriented in the machine direction and generally spaced apart from adjacent bond lines 51 by about 0.20 inch to about 0.90 inch, desirably about 0.25 inch to about 0.820 inch.

Alternatively, the nonwoven web 12 may be through-air-bonded to produce the thermally stabilized creped nonwoven web 12. In accordance with this embodiment of the invention, the nonwoven web 12 desirably is made of bicomponent or multicomponent fibers wherein the polymer components have different melting points. For example, the bicomponent fibers may have a propylene/ethylene random copolymer component and a polypropylene polymer component in one of several different arrangements, including a side-by-side arrangement and a sheath/core arrangement. Any suitable polymers or polymer blends having different melting temperatures may be used to form the bicomponent fibers of this invention.

After the bicomponent nonwoven web 12 is creped as discussed above, the bicomponent nonwoven web 12 is passed through a through-air bonder to thermally stabilize the creped bicomponent nonwoven web 12. Within the through-air-bonder, heated air is forced through the nonwoven web 12. The air is heated to a temperature greater than a melting temperature of one polymer component but less than a melting temperature of the other polymer component. As a result of the passage of heated air though the nonwoven web 12, the lower melting polymer component melts to form interfiber bonds and thus, the nonwoven web 12 is thermally stabilized.

The through-air-bonding thermal stabilization process may be desirable to other post-crepe thermal stabilization processes because it does not subject the creped nonwoven web to any compression force or pressure during the process, as does the embossing thermal stabilization process. Thus, cross-direction oriented micropleats formed in the nonwoven web 12 during the creping process are less likely to be damaged during the through-air-bonding thermal stabilization process.

The thermally stabilized creped nonwoven web 12 has low density, high permeability, excellent surface and bulk softness, recoverable stretch properties, surface topology, and permanent out-of-plane fiber orientation. The stabilized creped nonwoven web 12 can be used in a variety of end products including liners, transfer and surge layers, outercovers, wipers, and other fluid handling materials.

One suitable use of the stabilized creped nonwoven web 12 is as an outercover component for a diaper. The stabilized creped nonwoven web 12 may, for instance, be laminated to a breathable polyolefin film including a mixture of thermoplastic polymer, e.g. a polyolefin such as polyethylene or polypropylene, and a particulate filler, e.g. calcium carbonate. The film is permeable to water vapor but substantially impermeable to liquid water. The breathable film can be laminated to the stabilized creped nonwoven web 12 using thermal bonding, adhesive bonding, and/or other bonding techniques well known in the art. The laminate is then positioned on the underside or backside of the absorbent core of a diaper with the film component facing the absorbent core. The creped nonwoven web component thus faces outward, contributing a soft, fluffy, bulky feel to the diaper.

Because of the looping caused in the uncreped, unbonded regions, the stabilized creped nonwoven web 12 is also highly suitable for use as the female ("loop") component in a hook-and-loop type fastener. The loops in the nonwoven web 12 engage the male fastener components in a peelable fashion, such that the hook and loop fastener can be opened and closed a number of times.

Test Methods

The density of a material is calculated by dividing the weight per unit area of a sample in grams per square meter (gsm) by the material caliper. A total of five samples are evaluated and averaged for the density value. Density is usually reported in units of grams/cubic centimeter (g/cc).

Permeability ($cm^2$ or darcy) is obtained from a measurement of the resistance by the material to the flow of liquid. A liquid of known viscosity is forced through the material of a given thickness at a constant flow rate and the resistance to flow, measured as a pressure drop, is monitored. Darcy's law is used to determine permeability as follows:

$$\text{Permeability} = \frac{\text{flow rate} \times \text{thickness} \times \text{viscosity}}{\text{pressure drop}} \quad \text{Eq. (2)}$$

where the units are:

permeability: $cm^2$ or darcy 1 darcy=$9.87 \times 10^{-9}$ $cm^2$ flow rate: cm/sec viscosity: pascal-sec pressure drop: pascal The apparatus consists of an arrangement wherein a piston within a cylinder pushes liquid through the sample to be measured. The sample is clamped between two aluminum cylinders with the cylinders oriented vertically. Both cylinders have an outside diameter of 3.5 inches, an inside diameter of 2.5 inches and a length of about 6 inches. The 3 inch diameter web sample is held in place by its outer edges and hence is completely contained within the apparatus. The bottom has a piston that is capable of moving vertically within the cylinder at a constant velocity and is connected to a pressure transducer that is capable of monitoring the pressure encountered by a column of liquid supported by the piston. The transducer is positioned to travel with the piston such that there is no additional pressure measured until the liquid column contacts the sample and is pushed through it. At this point, the additional pressure measured is due to the resistance of the material to liquid flow through it.

The piston is moved by a slide assembly that is driven by a stepper motor. The test starts by moving the piston at a constant velocity until the liquid is pushed through the sample. The piston is then halted and the baseline pressure is noted. This corrects for sample buoyancy effects. The movement is then resumed for a time adequate to measure the new pressure. The difference between the two pressures is the pressure due to the resistance of the material to liquid flow and is the pressure drop used in Eq. (1). The velocity of the piston is the flow rate. Any liquid of known viscosity can be used, although a liquid that wets the material is preferred since this ensures that saturated flow is achieved. The measurements were carried out using a piston velocity of 20 cm/min, mineral oil (Peneteck Technical Mineral Oil manufactured by Penreco of Los Angeles, Calif.) having a viscosity of 6 centipoise.

EXAMPLE 1

A creped spunbond web having a creped basis weight of about 0.75 osy was produced with a Ramisch primary bond pattern. The following samples were achieved using an embossing process for stabilizing the creped spunbond web. Three different samples were produced using different embossing patterns, including a sine-wave pattern; a MD line pattern; and a cross-star pattern. A fourth sample was provided wherein a spunbond nonwoven web was creped but not thermally stabilized. Each sample was tested for density, permeability, and pressure. Table 1 below compares the four samples with regard to density, permeability and pressure.

Figure 7:
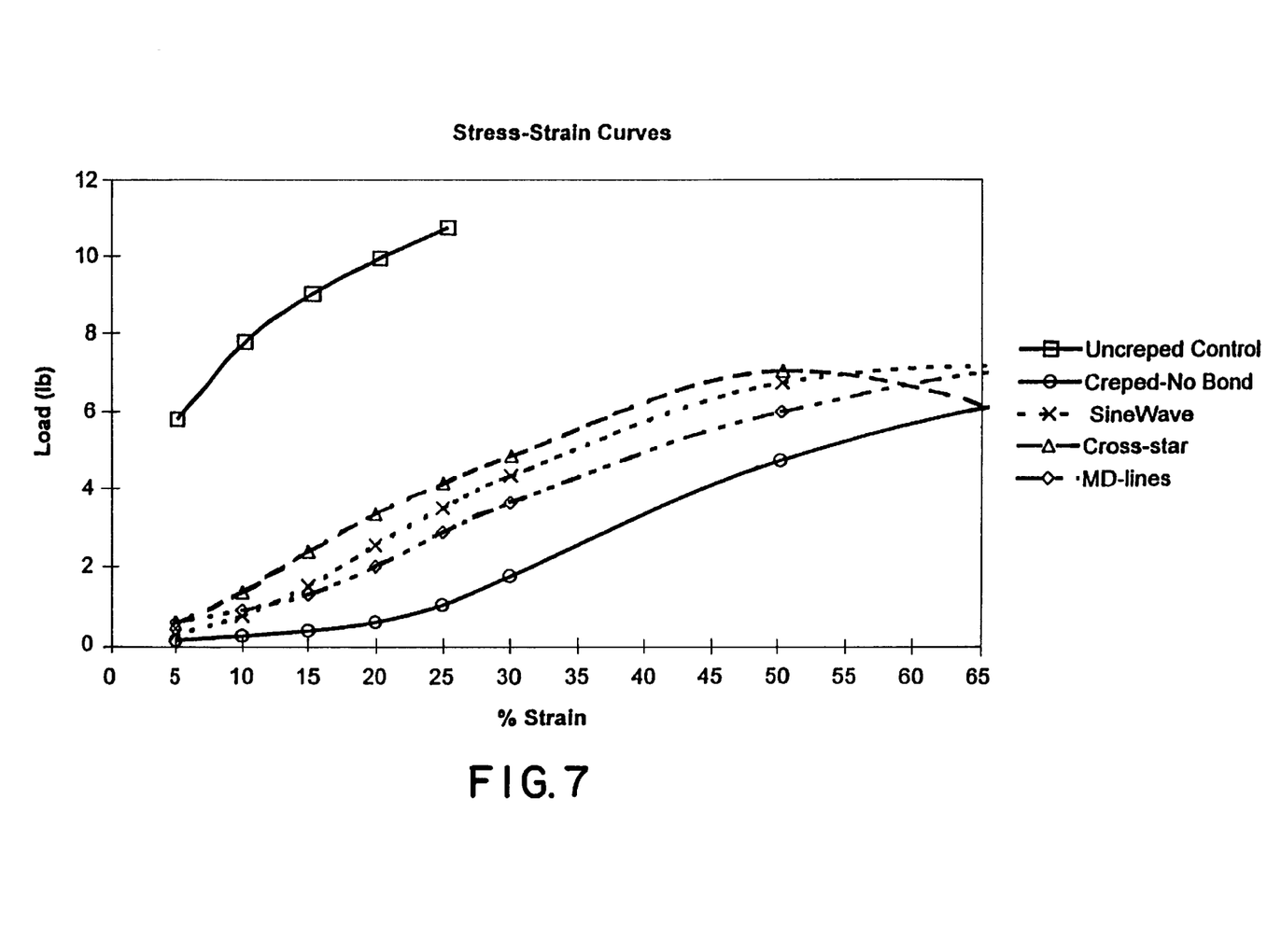
FIG. 7 illustrates load-strain curves for several sample stabilized creped nonwoven webs produced in accordance with one embodiment of this invention and compared to a load-strain curve for an uncreped control nonwoven web.

FIG. 7 illustrates the enhanced tensile strength of a creped spunbond web thermally stabilized using the embossing process according to this invention. As shown in FIG. 7, the stabilized creped nonwoven web 12 produced in accordance with this invention is capable of withstanding a load of at least about 2.0 lbs. at about 20% strain and a load of at least about 5.0 lbs. at about 50% strain. In comparison, an uncreped nonwoven web control is capable of withstanding a load of about 10.0 lbs. at about 20% strain and an unstabilized creped nonwoven web is capable of withstanding a load of about 0.5 lbs. at 20% strain and a load of less than about 5.0 lbs. at 50% strain.

TABLE 1

|  | Density (g/cc) | Permeability (darcies) | Pressure (Pascals) |
|---|---|---|---|
| Sine-Wave Pattern | | | |
| | 0.027 | 3766 | |
| | 0.028 | 3704 | 3.9 |
| | 0.026 | 3425 | 3.9 |
| | 0.028 | 4823 | 3.1 |
| | 0.029 | 4007 | 3.7 |
| Average | 0.028 | 3945 | 3.7 |
| St. Dev. | 0.001 | 533 | 0.4 |
| MD Line Pattern | | | |
| | 0.029 | 3258 | 4.6 |
| | 0.027 | 2867 | 4.8 |
| | 0.029 | 3828 | 3.9 |

TABLE 1-continued

|  | Density (g/cc) | Permeability (darcies) | Pressure (Pascals) |
|---|---|---|---|
|  | 0.025 | 2724 | 4.7 |
|  | 0.030 | 3735 | 4.1 |
| Average | 0.028 | 3282 | 4.4 |
| St. Dev. | 0.002 | 497 | 0.4 |
| Cross-Stars Pattern | | | |
|  | 0.025 | 2648 | 4.9 |
|  | 0.026 | 2931 | 4.6 |
|  | 0.026 | 2936 | 4.6 |
|  | 0.026 | 2796 | 4.8 |
|  | 0.024 | 2246 | 5.5 |
| Average | 0.025 | 2711 | 4.9 |
| St. Dev. | 0.001 | 285.676 | 0.4 |
| Unstabilized Creped Nonwoven Web | | | |
|  | 0.041 | 6935 | 3.1 |
|  | 0.044 | 7165 | 3.2 |
|  | 0.041 | 8240 | 2.6 |
|  | 0.038 | 7213 | 2.7 |
|  | 0.038 | 5948 | 3.3 |
| Average | 0.040 | 7100 | 2.98 |
| St. Dev. | 0.003 | 817 | 0.3 |

EXAMPLE 2

A 3.5 dpf creped spunbond web having a creped basis weight of about 0.4 osy was produced with a wire weave primary bond pattern. The spunbond web was creped to about 41% as it was removed from the drying drum. However, the final level of creping was about 36% as the creped spunbond web was wound onto a storage roll. The spunbond web was creped using an adhesive material available from the Air Products Adhesive Co., located in Allentown, Pa., under the trade designation A105.

The creped spunbond web was thermally stabilized using an embossing process in accordance with this invention. During the embossing process, a minimal draw speed of about 75–77 feet per minute ("fpm") and a bonding nip pressure of about 17 pounds per square inch ("psi") or 61.1 pounds per lineal inch ("PLI") were used. Seven codes or samples were thermally embossed using a MD line embossing pattern having about 12% pattern bond area. The pattern roll and the anvil roll each were set at and heated to varying temperatures. Table 2 below shows the set temperatures and the actual surface temperatures of the pattern roll and the anvil roll used to pattern emboss each of the seven samples. An eighth sample was not pattern embossed.

Figure 8:
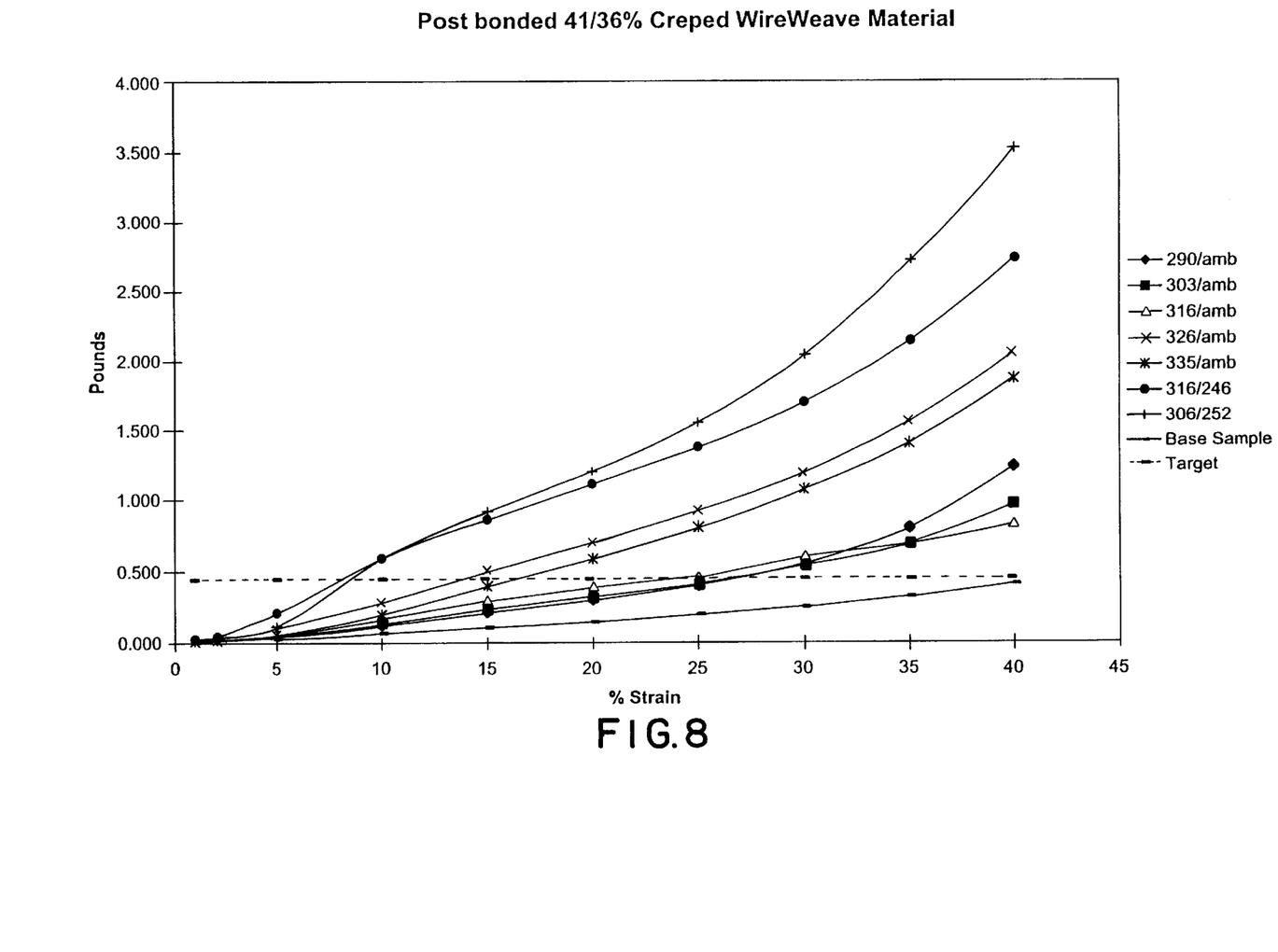
FIG. 8 illustrates load-strain curves for several sample stabilized creped nonwoven webs produced in accordance with one embodiment of this invention and compared to a load-strain curve for an uncreped control nonwoven web.

FIG. 8 illustrates the enhanced tensile strength of a creped spunbond web thermally stabilized using the embossing process according to this invention. As shown in FIG. 8, the post-crepe thermally stabilized samples have an increased modulus as compared to the unstabilized sample no. 8. Sample nos. 6 and 7 achieved a targeted 0.15 pli at about 7% to about 8% strain. Other post-crepe thermally stabilized samples reached the targeted pli at about 14% to about 28% strain. The unstabilized sample no. 8 did not reach the targeted 0.15 pli until after 40% strain. The 0.15 pli was chosen as the targeted pli because it is believed that this value represents the tension experienced during the embossing process and, thus, the material must be able to withstand a tension of 0.15 pli. The peak strain is increased and the targeted 0.15 pli is achieved at lower % strain due to the thermal stabilization.

TABLE 2

SURFACE TEMPERATURE DURING THERMAL STABILIZATION

| Code | Anvil Roll Set Temp. (° F.) | Actual Surface Temp. (° F.) | Anvil Roll Set Temp. (° F.) | Actual Surface Temp. (° F.) | Notes |
|---|---|---|---|---|---|
| 1 | 310 | 290 |  | ambient |  |
| 2 | 320 | 303 |  | ambient |  |
| 3 | 330 | 316 |  | ambient |  |
| 4 | 340 | 326 |  | ambient | slightly overbonded |
| 5 | 350 | 335 |  | ambient | severely overbonded |
| 6 | 330 | 316 | 280 | 246 | slightly overbonded |
| 7 | 320 | 306 | 280 | 252 |  |
| 8 |  |  |  |  |  |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto.

We claim:

1. A method for producing a stabilized creped nonwoven web, the method comprising the steps of:
    providing a nonwoven web;
    primarily bonding the nonwoven web;
    creping the primarily bonded nonwoven web; and
    forming an embossing pattern on the creped nonwoven web to produce the stabilized creped nonwoven web that is capable of withstanding a tensile force in a machine direction of at least about 2.0 pounds at about 20% strain.

2. The method of claim 1, further comprising the step of winding the stabilized creped nonwoven web onto a storage roll.

3. The method of claim 1, further comprising passing the creped nonwoven web through a s-wrap system before stabilizing the creped nonwoven web.

4. The method of claim 1, wherein the nonwoven web provided comprises a spunbond nonwoven web.

5. The method of claim 4, wherein the creped nonwoven web has a basis weight of about 0.50 osy to about 1.0 osy.

6. The method of claim 1, wherein the creping step produces a creped nonwoven web having a crepe level of at least 5%.

7. The method of claim 1, wherein the nonwoven web is primarily bonded using a Ramisch primary bond pattern.

8. A method for producing a stabilized creped spunbond nonwoven web, the method comprising the steps of:
    producing a spunbond nonwoven web;
    bonding the spunbond nonwoven web;
    creping the spunbond nonwoven web; and
    applying an embossing pattern to the creped spunbond nonwoven web to produce the stabilized creped spunbond nonwoven web that is capable of withstanding a tensile force in a machine direction of at least about 2.0 pounds at about 20% strain.

9. The method of claim 8 wherein the spunbond nonwoven web is primarily bonded using a calender.

10. The method of claim 8, wherein a low bond area pattern is used during the embossing step.

11. The method of claim 8, wherein the embossing step generates a plurality of embossed areas, said embossed areas being continuous in the machine direction.

12. The method of claim 8, wherein during the embossing step, a cross-stars patter is used to produce the stabilized creped spunbond nonwoven web.

13. The method of claim 8, wherein during the embossing step, a sine-wave pattern is used to produce the stabilized spunbond nonwoven web.

14. The method of claim 8, wherein during the embossing step, a machine direction line pattern is used to produce the stabilized creped spunbond nonwoven web.

15. The method of claim 8, wherein the stabilized creped spunbond nonwoven web has a density of at least about 0.20 g/cc.

16. The method of claim 8, wherein the stabilized creped spunbond nonwoven web has a density of about 0.24 g/cc to about 0.30 g/cc.

17. The method of claim 8, wherein the stabilized creped spunbond nonwoven web has a permeability of at least about 2200 darcies.

18. The method of claim 8, wherein the stabilized creped spunbond nonwoven web has a permeability of about 2200 darcies to about 4900 darcies.

* * * * *